United States Patent
Dorsel et al.

(10) Patent No.: US 7,205,553 B2
(45) Date of Patent: Apr. 17, 2007

(54) READING MULTI-FEATURED ARRAYS

(75) Inventors: Andreas N. Dorsel, Menlo Park, CA (US); Glenda C. Delenstarr, Belmont, CA (US); Kenneth L. Staton, San Carlos, CA (US); George P. Tsai, San Jose, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 497 days.

(21) Appl. No.: 10/881,688

(22) Filed: Jun. 29, 2004

(65) Prior Publication Data

US 2005/0029468 A1 Feb. 10, 2005

Related U.S. Application Data

(62) Division of application No. 09/846,125, filed on Apr. 30, 2001, now Pat. No. 6,756,202.

(51) Int. Cl.
*G01N 21/64* (2006.01)

(52) U.S. Cl. .................................................. 250/458.1

(58) Field of Classification Search .............. 250/458.1
See application file for complete search history.

(56) References Cited

U.S. PATENT DOCUMENTS

| 5,675,443 | A | 10/1997 | Dorsel |
| 5,763,870 | A | 6/1998 | Sadler et al. |
| 5,837,475 | A | 11/1998 | Dorsel et al. |
| 5,891,739 | A | 4/1999 | Berndt |
| 5,945,670 | A | 8/1999 | Rudeen |
| 6,646,271 | B2 * | 11/2003 | Yokokawa et al. ...... 250/458.1 |

\* cited by examiner

*Primary Examiner*—David Porta
*Assistant Examiner*—Christopher Webb

(57) ABSTRACT

A method, apparatus, and computer program product for reading fluorescence signals from an array of chemical moieties (such as different sequence peptides or polynucleotides, for example different DNA sequences). In the method the spatial sequence of scanned locations need not be the same as the temporal sequence. For example, a later illuminated line may be spatially closer to an earlier illuminated line than is a temporally intervening illuminated line.

19 Claims, 4 Drawing Sheets

READING MULTI-FEATURED ARRAYS

CROSS-REFERENCE TO RELATED APPLICATIONS

This application is a divisional application of application Ser. No. 09/846,125 filed on Apr. 30, 2001 and now issued as U.S. Pat. No. 6,756,202; the disclosure of which is herein incorporated by reference.

FIELD OF THE INVENTION

This invention relates to arrays, particularly biopolymer arrays such as DNA or protein arrays, which are useful in diagnostic, screening, gene expression analysis, and other applications.

BACKGROUND OF THE INVENTION

Polynucleotide arrays (such as DNA or RNA arrays) and peptide array, are known and may be used, for example, as diagnostic or screening tools. Such arrays include regions (sometimes referenced as spots or features) of usually different sequence polynucleotides or peptides arranged in a predetermined configuration on a substrate. The array is "addressable" in that different features have different predetermined locations ("addresses") on a substrate carrying the array.

Biopolymer arrays can be fabricated using in situ synthesis methods or deposition of the previously obtained biopolymers. The in situ fabrication methods include those described in U.S. Pat. No. 5,449,754 for synthesizing peptide arrays, and in U.S. Pat. No. 6,180,351 and WO 98/41531 and the references cited therein for polynucleotides. In situ methods also include photolithographic techniques such as described, for example, in WO 91/07087, WO 92/10587, WO 92/10588, and U.S. Pat. No. 5,143,854. The deposition methods basically involve depositing biopolymers at predetermined locations on a substrate which are suitably activated such that the biopolymers can link thereto. Biopolymers of different sequence may be deposited at different feature locations on the substrate to yield the completed array. Procedures known in the art for deposition of polynucleotides, particularly DNA such as whole oligomers or cDNA, are described, for example, in U.S. Pat. No. 5,807,522 (touching drop dispensers to a substrate), and in PCT publications WO 95/25116 and WO 98/41531, and elsewhere (use of an ink jet type head to fire drops onto the substrate).

In array fabrication, the quantities of DNA available for the array are usually very small and expensive. Sample quantities available for testing are usually also very small and it is therefore desirable to simultaneously test the same sample against a large number of different probes on an array. These conditions require the manufacture and use of arrays with large numbers of very small, closely spaced features.

The arrays, when exposed to a sample, will exhibit a binding pattern. The array can be read by observing this binding pattern by, for example, labeling all targets such as polynucleotide targets (for example, DNA), in the sample with a suitable label (such as a fluorescent compound), scanning an illuminating beam across the array and accurately observing the fluorescent signal from the different features of the array. Assuming that the different sequence polynucleotides were correctly deposited in accordance with the predetermined configuration, then the observed binding pattern will be indicative of the presence and/or concentration of one or more polynucleotide components of the sample. Peptide or arrays of other chemical moieties can be used in a similar manner. Techniques and apparatus for scanning chemical arrays are described, for example, in U.S. Pat. No. 5,763,870 and U.S. Pat. No. 5,945,679. Apparatus which reads an array by scanning an illuminating beam by the foregoing technique are often referred to as scanners and the technique itself often referred to as scanning.

Array scanners typically use a laser beam as a light source, which is scanned over the array features. A detector (typically a fluorescence detector) with a very high light sensitivity is normally desirable to achieve maximum signal-to-noise in detecting hybridized molecules, particularly in array scanners used for DNA sequencing or gene expression studies. At present, photomultiplier tubes ("PMTs") are still the detector of choice although charge coupled devices ("CCDs") can also be used. PMTs are typically used for temporally sequential scanning of array features, while CCDs permit scanning many features in parallel (for example, one line of features simultaneously, in which case an illuminating line may be used).

During scanning of an array, triplet saturation occurs. That is, fluorescent species are normally excited to a state from which they return to the singlet ground state while emitting the fluorescent light. However, the excited species has a finite probability of ending up in a lowest triplet state. Species in the triplet state do not emit fluorescence and thus are lost to producing a fluorescent signal while remaining in that state. Unfortunately, such triplet states may have very long lifetimes. Saturation is discussed in more detail, for example, in U.S. Pat. No. 5,945,679. As any region containing a fluorescent species may undergo multiple excitations during scanning, an increasing proportion will be unavailable to produce a signal due to saturation. A known solution to this problem is to re-scan a line on the array after waiting for a sufficient time for the fluorescent species to recover from saturation. However, the present invention realizes that for an array containing thousands of features, this may lengthen the scanning process. Furthermore, the present invention realizes that other problems may arise depending upon the scanning pattern. For example, in a rectangular scanning pattern a line is scanned from a first end to a second, and the next line is scanned from the second end to the first, and the process repeated for subsequent lines in turn. In this pattern, the time that a location has to recover from saturation is shorter toward the beginning and end of a scan line than at the center. The present invention realizes that this may lead to incomplete recovery from saturation and thus to a non-uniformity in detected signals from a uniform array.

It would be desirable then, to provide a means to scan an array in which the effect of saturation can be at least reduced.

SUMMARY OF THE INVENTION

The present invention then, provides a method of reading fluorescence signals from an array of chemical moieties (such as different sequence peptides or polynucleotides, for example different DNA sequences). In one such method multiple locations on the array are illuminated and any resulting fluorescence from the array is detected. In this case a later illuminated location is spatially closer to an earlier illuminated location than is a temporally intervening illuminated location lying on a same line as the later and earlier illuminated locations. This procedure may be repeated in one or more further cycles as required and using other locations, until the array or a desired portion of it has been read. Alternatively, multiple paths across the array may be illuminated and any resulting fluorescence from the array is detected. In such case the paths extend in a same lengthwise direction and are spaced from one another in a crosswise direction, and the spatial sequence of the paths does not correspond to their temporal sequence. For example, at least one later illuminated path may be closer to an earlier illuminated path than a temporally intervening illuminated path. The multiple paths may be parallel lines.

In the method, one or more later illuminated locations or paths may be interleaved between one or more previously illuminated locations or paths. The time between illuminating a location or path and illuminating a closest later illuminated location or path, may be selected based on a saturation characteristic of a fluorophore producing the fluorescence. Alternatively, the time may be based on an identifier associated with the array (such as being carried on an array substrate or a housing for the array), or on a spatial distribution of the illumination and a pixel size during the detecting.

Spacings of illuminated locations can be selected between any of the locations as desired. For example, the spacing between the spatially nearest locations or paths of the earlier, temporally intervening, and interleaved locations or paths may be equal. Further, various illumination techniques can be used within the methods of the present invention. For example, when the paths are lines they may be illuminated by scanning a light beam along them. As another example, timewise successively illuminated lines during any one cycle may be illuminated by scanning a light beam in the same or in opposite directions. The present invention further provides an apparatus which can execute a method of the present invention. The apparatus includes an illumination source to cause fluorescence of the chemical moieties. A scan system directs the illumination source to different locations on the array, while a detector detects any resulting fluorescence from the array. A processor controls the scan system to obtain the illumination of a method of the present invention. A computer program product for use with an apparatus, for reading fluorescence signals from an array of chemical moieties, is also provided to execute the steps of a method of the present invention.

While the methods and apparatus have been described in connection with arrays of various moieties, such as polynucleotides or DNA, other moieties can include any chemical moieties such as biopolymers.

The present invention can provide any one or more of the following or other benefits. For example, an array can be scanned such that loss of signal from saturation effects is kept low, or maintained at similar levels during the array scanning process.

BRIEF DESCRIPTION OF THE DRAWINGS

Embodiments of the invention will now be described with reference to the drawings, in which.

To facilitate understanding, the same reference numerals have been used, where practical, to designate similar elements that are common to the FIGS.

DETAILED DESCRIPTION OF THE INVENTION

Figure 1:
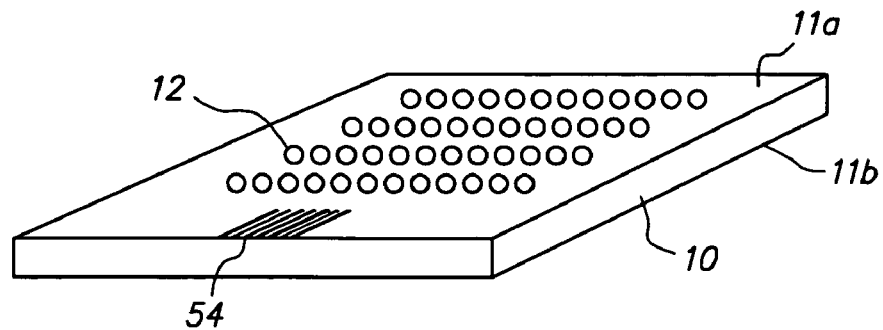
FIG. 1 is a perspective view of a substrate carrying a typical array, as may be used with, or part of, a package of the present invention.

In the present application, unless a contrary intention appears, the following terms refer to the indicated characteristics. A "biopolymer" is a polymer of one or more types of repeating units. Biopolymers are typically found in biological systems and particularly include polysaccharides (such as carbohydrates), and peptides (which term is used to include polypeptides and proteins) and polynucleotides as well as their analogs such as those compounds composed of or containing amino acid analogs or non-amino acid groups, or nucleotide analogs or non-nucleotide groups. This includes polynucleotides in which the conventional backbone has been replaced with a non-naturally occurring or synthetic backbone, and nucleic acids (or synthetic or naturally occurring analogs) in which one or more of the conventional bases has been replaced with a group (natural or synthetic) capable of participating in Watson-Crick type hydrogen bonding interactions. Polynucleotides include single or multiple stranded configurations, where one or more of the strands may or may not be completely aligned with another. A "nucleotide" refers to a sub-unit of a nucleic acid and has a phosphate group, a 5 carbon sugar and a nitrogen containing base, as well as functional analogs (whether synthetic or naturally occurring) of such sub-units which in the polymer form (as a polynucleotide) can hybridize with naturally occurring polynucleotides in a sequence specific manner analogous to that of two naturally occurring polynucleotides. For example, a "biopolymer" includes DNA (including cDNA), RNA, oligonucleotides, and PNA and other polynucleotides as described in U.S. Pat. No. 5,948,902 and references cited therein (all of which are incorporated herein by reference), regardless of the source. An "oligonucleotide" generally refers to a nucleotide multimer of about 10 to 100 nucleotides in length, while a "polynucleotide" includes a nucleotide multimer having any number of nucleotides. A "biomonomer" references a single unit, which can be linked with the same or other biomonomers to form a biopolymer (for example, a single amino acid or nucleotide with two linking groups one or both of which may have removable protecting groups). A biomonomer fluid or biopolymer fluid reference a liquid containing either a biomonomer or biopolymer, respectively (typically in solution).

An "array", unless a contrary intention appears, includes any one-, two- or three-dimensional arrangement of addressable regions bearing a particular chemical moiety or moieties (for example, biopolymers such as polynucleotide sequences) associated with that region. An array is "addressable" in that it has multiple regions of different moieties (for example, different polynucleotide sequences) such that a region (a "feature" or "spot" of the array) at a particular predetermined location (an "address") on the array will detect a particular target or class of targets (although a feature may incidentally detect non-targets of that feature). Array features are typically, but need not be, separated by intervening spaces. In the case of an array, the "target" will be referenced as a moiety in a mobile phase (typically fluid), to be detected by probes ("target probes") which are bound to the substrate at the various regions. However, either of the "target" or "target probes" may be the one which is to be evaluated by the other (thus, either one could be an unknown mixture of polynucleotides to be evaluated by binding with the other). An "array layout" refers collectively to one or more characteristics of the features, such as feature positioning, one or more feature dimensions, and some indication of a moiety at a given location. "Hybridizing" and "binding", with respect to polynucleotides, are used interchangeably.

When one item is indicated as being "remote" from another, this is referenced that the two items are at least in different buildings, and may be at least one mile, ten miles, or at least one hundred miles apart. "Communicating" information references transmitting the data representing that information as electrical signals over a suitable communication channel (for example, a private or public network). "Forwarding" an item refers to any means of getting that item from one location to the next, whether by physically transporting that item or otherwise (where that is possible) and includes, at least in the case of data, physically transporting a medium carrying the data or communicating the data. An array "package" may be the array plus only a substrate on which the array is deposited, although the package may include other features (such as a housing with a chamber). A "chamber" references an enclosed volume (although a chamber may be accessible through one or more ports). It will also be appreciated that throughout the present application, that words such as "top", "upper", and "lower" are used in a relative sense only. A "location" refers to any finite small area on the array that can be illuminated and any resulting fluorescence therefrom simultaneously (or shortly thereafter) detected, for example a pixel. "Timewise" and "temporally" are used synonymously to indicate relationship in time. Thus, events which are temporally sequential follow one after the other in time, whereas items which are spatially sequential follow one after the other in space. A "processor" references any combination of hardware or software which can control components as required to execute recited steps and includes, for example, a general purpose digital microprocessor suitably programmed (for example, from a computer readable medium carrying necessary program code or by communication from a remote location) to perform all of the steps required of it, or any hardware or software combination which will perform those or equivalent steps. Reference to a singular item, includes the possibility that there are plural of the same items present. All patents and other references cited in this application, are incorporated into this application by reference except insofar as where any definitions in those references conflict with those of the present application (in which case the definitions of the present application are to prevail).

Figure 2:
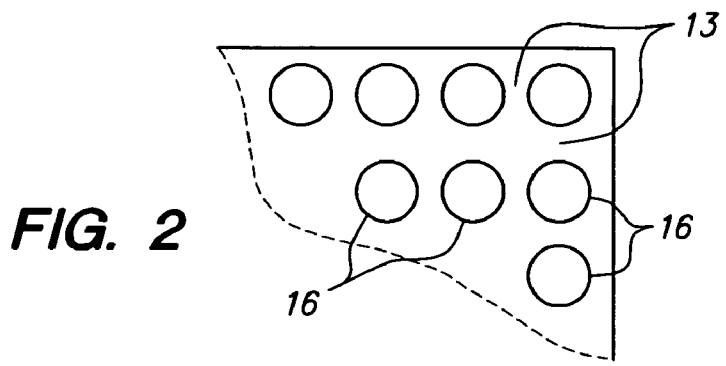
FIG. 2 is an enlarged view of a portion of FIG. 1 showing some of the identifiable individual regions of a single array of FIG. 1.
Figure 3:
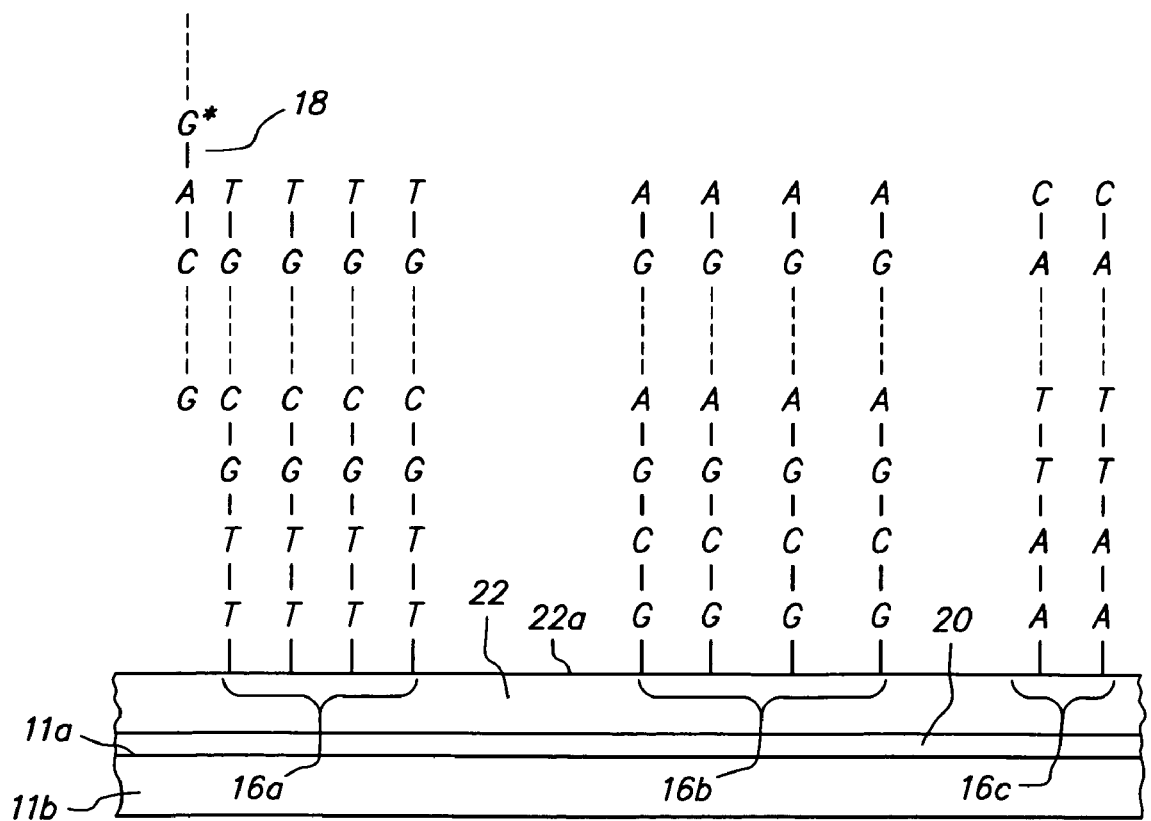
FIG. 3 is an enlarged cross-section of a portion of FIG. 2.

Referring first to FIGS. 1–3, a contiguous planar transparent substrate 10 carries multiple features 16 disposed across a first surface 11a of substrate 10 and separated by areas 13. Features 16 are disposed in a pattern which defines the array. A second surface 11b of substrate 10 does not carry any features. Substrate 10 may be of any shape although the remainder of the package of the present invention may need to be adapted accordingly. A typical array may contain at least ten features 16, or at least 100 features, at least 1,000, at least 100,000 features, or more. All of the features 16 may be of different composition, or some or all could be the same. Each feature carries a predetermined moiety or mixture of moieties which in the case of FIGS. 1–3 is a polynucleotide having a particular sequence. This is illustrated schematically in FIG. 3 where regions 16 are shown as carrying different polynucleotide sequences. Features 16 may have widths (that is, diameter, for a round spot) in the range from a minimum of about 10 µm to a maximum of about 1.0 cm. In embodiments where very small spot sizes or feature sizes are desired, features 16 may have widths in the range of about 1.0 µm to 1.0 mm, usually about 5.0 µm to 500 µm, and more usually about 10 µm to 200 µm. Arrays of FIGS. 1–3 can be manufactured by in situ or deposition methods as discussed above. In use, a feature can detect a polynucleotide of a complementary sequence by hybridizing to it, such as polynucleotide 18 being detected by feature 16a in FIG. 3 (the "*" on polynucleotide 18 indicating a label such as a fluorescent label). Use of arrays to detect particular moieties in a sample (such as target sequences) are well known.

Figure 4:
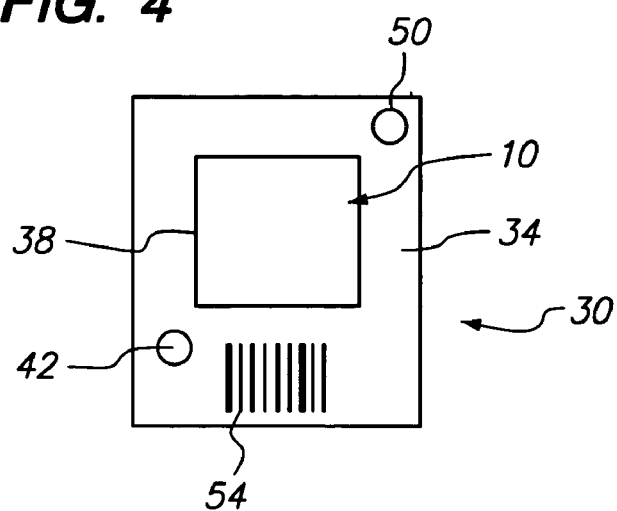
FIG. 4 is a front view of an array package in the form of a cartridge.

Referring now to FIG. 4 an array package 30 may include a housing 34 which has received substrate 10 adjacent an opening. Substrate 10 is sealed (such as by the use of a suitable adhesive) to housing 34 around a margin 38 with the second surface 11b facing outward. Housing 34 is configured such that housing 34 and substrate 10, define a chamber into which features 16 of array 12 face. This chamber is accessible through resilient septa 42, 50 which define normally closed ports of the chamber. Array package 30 preferably includes an identification ("ID") 54 of the array (sometimes referenced herein as an "identifier"). The identifier 54 may be in the form of a bar code or some other machine readable code applied during the manufacture of array package 30. Identifier 54 may itself contain information on a saturation characteristic of the fluorescent label (a fluorophore) on target polynucleotide 18. This can be done, for example, either where it is known that a target in a sample to which an array of the type of array 12 is exposed, will likely contain a particular label, or where the array 12 was associated with a known target label in the form of a target labeling kit or associated with instructions to use a particular label. Throughout this application "association" of any these or other items with the array, can be accomplished, for example, by the items being present in the same package as the array when shipped to an end user. In an alternative procedure, identifier 54 may be simply a unique series of characters which is also stored in a local or remote database in association with the foregoing label saturation characteristic information. Such a database may be established by an array manufacturer and communicated to the user (from a remote, or local source such as on a portable storage medium associated with the array) for retrieval in response to providing the identifier 54.

It will be appreciated though, that other array packages may be used. For example, the array package may consist only of the array of features 16 on substrate 10 (in which case ID 54 can be applied directly to substrate 10). Thus, an array package need not include any housing or closed chamber.

The components of the embodiments of the package 30 described above, may be made of any suitable material. For example, housing 34 can be made of metal or plastic such as polypropylene, polyethylene or acrylonitrile-butadiene-styrene ("ABS"). Substrate 10 may be of any suitable material, and is preferably sufficiently transparent to the wavelength of an interrogating and array emitted light, as to allow interrogation without removal from housing 34. Such transparent and non-transparent materials include, for flexible substrates: nylon, both modified and unmodified, nitrocellulose, polypropylene, and the like. For rigid substrates, specific materials of interest include: glass; fused silica, silicon, plastics (for example, polytetrafluoroethylene, polypropylene, polystyrene, polycarbonate, and blends thereof, and the like); metals (for example, gold, platinum, and the like). The first surface 11a of substrate 10 may be modified with one or more different layers of compounds that serve to modify the properties of the surface in a desirable manner. Such modification layers, when present, will generally range in thickness from a monomolecular thickness to about 1 mm, usually from a monomolecular thickness to about 0.1 mm and more usually from a monomolecular thickness to about 0.001 mm. Modification layers of interest include: inorganic and organic layers such as metals, metal oxides, polymers, small organic molecules and the like. Polymeric layers of interest include layers of: peptides, proteins, polynucleic acids or mimetics thereof (for example, peptide nucleic acids and the like); polysaccharides, phospholipids, polyurethanes, polyesters, polycarbonates, polyureas, polyamides, polyethyleneamines, polyarylene sulfides, polysiloxanes, polyimides, polyacetates, and the like, where the polymers may be hetero- or homopolymeric, and may or may not have separate functional moieties attached thereto (for example, conjugated), The materials from which substrate 10 and housing 34 (at least the portion facing toward the inside of chamber 36) may be fabricated should ideally themselves exhibit a low level of binding during hybridization or other events.

Figure 5:
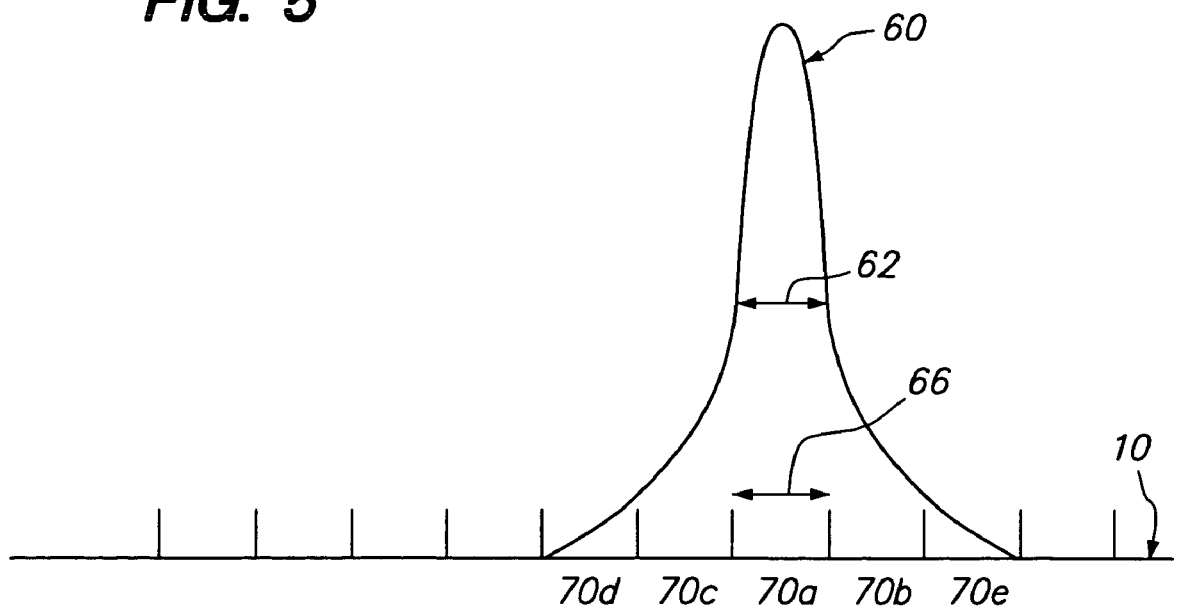
FIG. 5 illustrates a typical scanning beam spatial power distribution in relation to array features.

Referring to FIG. 5, a concept of the present invention is illustrated. In FIG. 5 power distribution 60 is a typical spatial power distribution curve of an illumination source in the form of a laser beam of circular cross-section focused onto an array 12. Power distribution 60 has a half-height width 62 of typically about 1–10 μm with each square pixel 70 detected by a detector having a width of from about one to ten times half-height width 62. This also illustrates a difficulty with conventional beam scanning schemes. In particular, in a typical scanning configuration a laser beam of FIG. 5 may be used to scan a row of pixels 70a (extending in and out of the page) and any resulting fluorescence signals from those pixels detected by a suitable detector. Conventionally the laser beam is then moved over a width of a pixel to a next row 70b of pixels to be detected, and is then moved along that row (that is, in a direction in or out of the paper) and any resulting signals detected. The pixel being detected by the detector is moved along with the beam in a known manner or as described below. This simultaneous beam and detection movement (often referenced together as "scanning", "scanned" and the like), is repeated moving from one row to the next adjacent row until the entire array 12 has been covered. However, the present invention recognizes that when a given row of pixels 70 is being scanned, other adjacent rows are being illuminated by the laser beam (although perhaps with lower power than the row being scanned and detected). For example, while row 70a in FIG. 5 is being scanned, 70b, 70e, 70c, 70d are also being simultaneously exposed to the laser beam (although no resulting fluorescence signal is being detected from them). This means that some percentage of fluorescent moieties in each of those adjacent rows will become lost to a triplet state. When pixels of the next adjacent row, for example row 70b, are scanned all of the fluorescent moieties therein may not have had sufficient time to return from a triplet to ground state. Thus, when those adjacent rows are scanned in turn, some of the fluorescent signal has already been lost to the triplet state (in addition to a portion which may be lost during the scanning of that adjacent row).

For ease of reference, as already pointed out "scanning" will often be used by itself in a manner which will be understood to include actually moving the illuminating source as needed and the detecting of the resulting fluorescence. Also, in FIGS. 6–10 the arrows indicate scanning directions across rows of pixels 70 with suffixes "a", "b", "c" and the like being used to indicate scanning order (the smaller case equivalent of "L" is not used as a suffix). Thus, in the conventional rectangular scanning pattern of FIG. 6 a row 70a is first scanned from left to right as viewed in the FIG. 7, the laser beam is then re-positioned at a next adjacent row 70b which is then scanned from right to left, then to 70c which is scanned from left to right, and so on.

Figure 6:
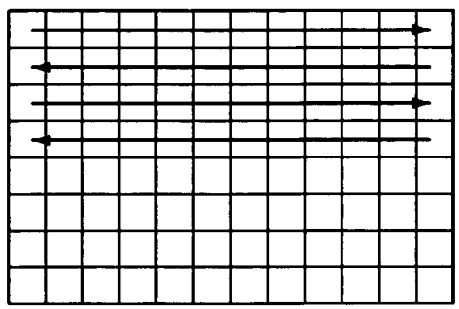
FIGS. 6 and 7 illustrate conventional array scanning patterns.
Figure 7:
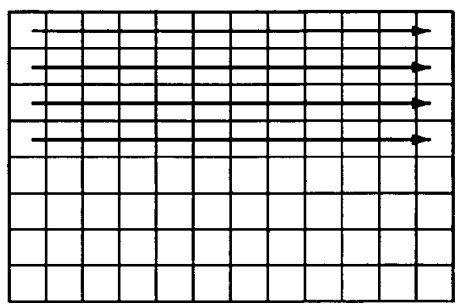

Referring to FIGS. 6 and 7 conventional scanning patterns are illustrated. Note from FIG. 6 then, that as described in connection with FIG. 5 while one row 70 (such as 70a) is being scanned, followed by a next adjacent row (such as 70b), the next adjacent row (such as 70b) is still being illuminated and some proportion of the species may be lost to the triplet state and not have had time to recover (that is, return from the triplet to the ground state) by the time that adjacent row (such as 70b) is then scanned. Even worse, the proportion that is still in the triplet state may vary along the length of a pixel row leading to non-uniformity in signals from pixels which otherwise might be uniform. For example, when row 70a is scanned from left to right, the rightmost pixel of row 70b has less time to recover than the leftmost pixel of row 70b, and thus the detected fluorescent signal from row 70b may increase from right to left even if conditions along row 70b are otherwise constant.

Referring to FIG. 7 a conventional zigzag scanning pattern is illustrate. In this pattern a row 70a is scanned from left to right, the beam then re-positioned back to the left hand side of row 70b to scan row 70b also from left to right, and this process repeated for all rows of pixels 70 to be scanned on the array. The laser beam may be turned off while being re-positioned from one row to the next adjacent row. Thus, in the zigzag scanning pattern all pixel rows are scanned in a same direction. While this pattern does not suffer from the same uniformity concerns as the rectangular pattern, time is wasted moving the laser from one end of one row back to the next end of an adjacent row. For an array with many rows (for example, one hundred), this can amount to a large amount of wasted time. Furthermore, as in the rectangular scanning pattern, some proportion of fluorophores in pixels of the adjacent row are still lost to the triplet state since there may be insufficient time for them to recover. In both FIGS. 6 and 7, the timewise sequence of the linear scanned paths is the same as the spatial sequence. That is, if one moves across the lines 70 in the order in which they spatially occur (70a, 70b, 70c, and so on), this is the same as their timewise order.

Figure 8:
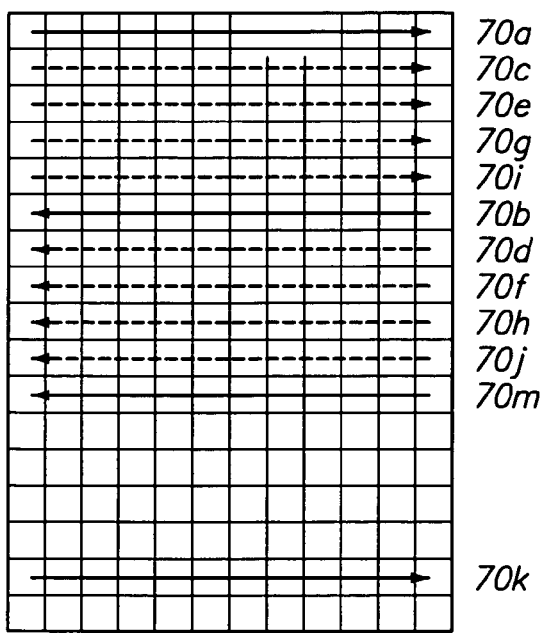
FIG. 8–10 illustrate methods of the present invention.

Referring to FIG. 8, a method of the present invention is illustrated. In the scanning pattern of FIG. 8 multiple parallel lines of pixels 70 on array 12 are illuminated by moving a focused laser beam across them and any resulting fluorescence detected (that is, the lines of pixels 70 are scanned). However, unlike FIGS. 6 and 7 the timewise sequence of the lines 70 in FIG. 8 (or FIG. 9 or 10) is no longer the same as their spatial sequence. In particular, in FIG. 8 it will be seen that multiple later illuminated lines (such as lines 70c, 70e, 70g, 70i) are all closer to an earlier illuminated line (such as line 70a) than a temporally intervening illuminated line (such as line 70b), and in fact those later illuminated lines (such as lines 70c, 70e, 70g, 70i) are interleaved between the earlier (such as 70a) and temporally intervening (such as 70b) illuminated lines. Note that in FIG. 8 a first cycle of scanning can be considered lines 70a through 70j, with a next cycle started by lines 70k, 70m (lines subsequent to 70m are repeated in a same pattern as 70c through 70j). Note that in this example (and in FIGS. 9 and 10), the spacing between all scan lines (including the nearest lines of the earlier, temporally intervening and interleaved lines) is equal. Also, it will be seen that in FIG. 8 (and in FIGS. 9 and 10) timewise successive scan lines of any cycle are illuminated scanned in opposite directions. However, while this opposite configuration saves time, it is not essential and timewise successive scan lines could be scanned in the same direction. The laser beam can be turned off so as not to provide any illumination at the array while it is being re-positioned between lines.

Figure 9:
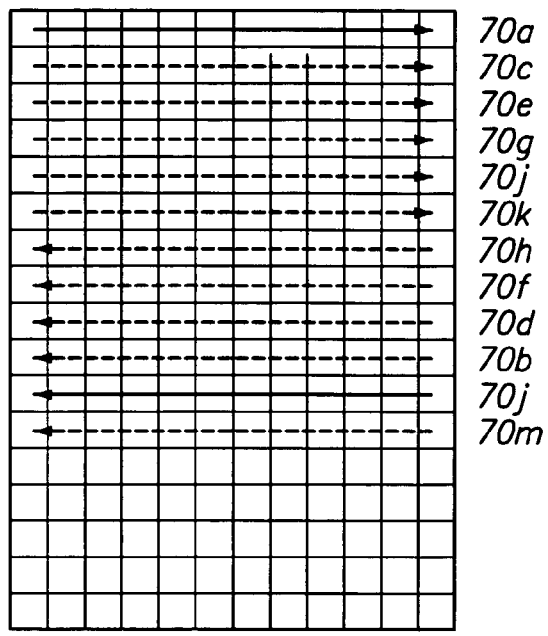
Figure 10:
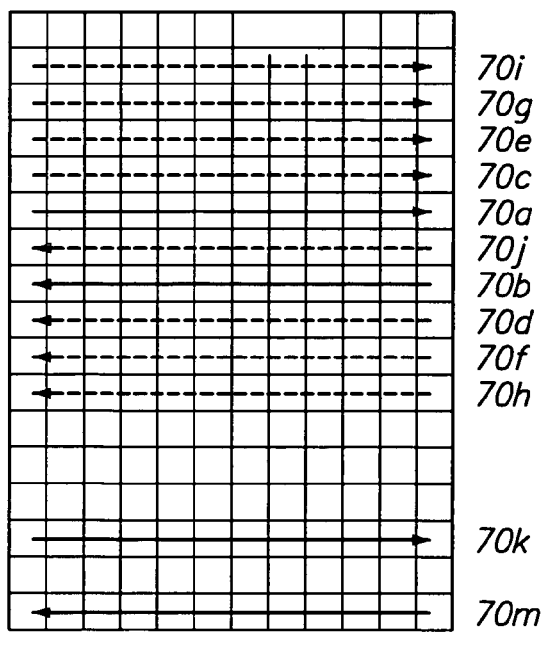

FIG. 9 illustrates a further scanning method of the present invention, wherein lines 70a through 70k represent one scanning cycle which may then be repeated starting in a new cycle with line 70m (subsequent lines not being shown). Similarly, lines 70a through 70k in FIG. 10 represent a cycle of a further scanning method of the present invention with lines 70a through 70j representing a first cycle and lines 70k, 70m being the first two lines of a next cycle which repeats the same pattern of the first cycle. It should be appreciated that while scanning is performed along lines as shown in FIGS. 8–10, this is not necessary. For example, other patterns could be used the same as in FIGS. 8–10 but wherein instead of the lines 70 (each of which also has multiple locations within it) could instead each be replaced with just a single location (that is, just single pixels; in this situation those locations would lie along a same line extending up and own as viewed in FIGS. 8–10). Further, paths other than straight lines could be used (for example, if array 12 had rows of semi-circular features, semi-circular scan paths could be used, although this would not be necessary).

Other scanning patterns within the present invention are possible. For example, assume spatially sequential rows on an array are numbered 1, 2, 3, 4, 5, 6 and so on to n (where n is an integer), from a top of the array down, and that L and R are used to indicate scanning from left to right, and right to left, respectively. One particular scanning pattern would include the following timewise sequence 1L, 6R, 3L, 8R, 5L, 10R and so on (that is, row 1 is scanned from left to right, then row 6 from right to left, then row three from left to right, then row 8 from right to left and so on). The foregoing scanning sequence can be generally represented as repeated cycles of scanning along row (2n−5)L followed by row (2n)R (where n starts at an integer, in this case 3, such that each scan line is a positive number), n increasing by 1 in each subsequent cycle. A variation of the foregoing then, would be (2n−9)L, (2n)R, or more generally (2n−a)L, (2n)R where a is any positive odd integer greater than 3. Again, n begins with a positive integer such that (2n−a) is positive, and increments by 1 in each cycle.

It will be appreciated that many other scanning patterns are possible within a method of the present invention. Which pattern may be considered best in a particular situation depends upon how much time is desired to elapse before a line spatially adjacent a previously scanned line is to elapse. In particular, a desired time between illuminating a line and illuminating a spatially closest later illuminated line can be evaluated. The desired time will depend on factors such as scan speed (higher scan speeds suggest greater spatial distance between temporally adjacent scan lines), laser beam power distribution at the array, pixel size, and a saturation characteristic (that is, what proportion will be excited to a triplet state and the rate of return therefrom to the ground state) of a fluorophore producing the fluorescence. Suitable scan patterns may then be calculated from known values, or can be readily determined experimentally. For example, using a test array which has a uniform fluorophore distribution thereon, scan patterns can be tested with increasing spatial distance between temporally adjacent scan lines until no further improvement in detected fluorescence signal is observed.

Figure 11:
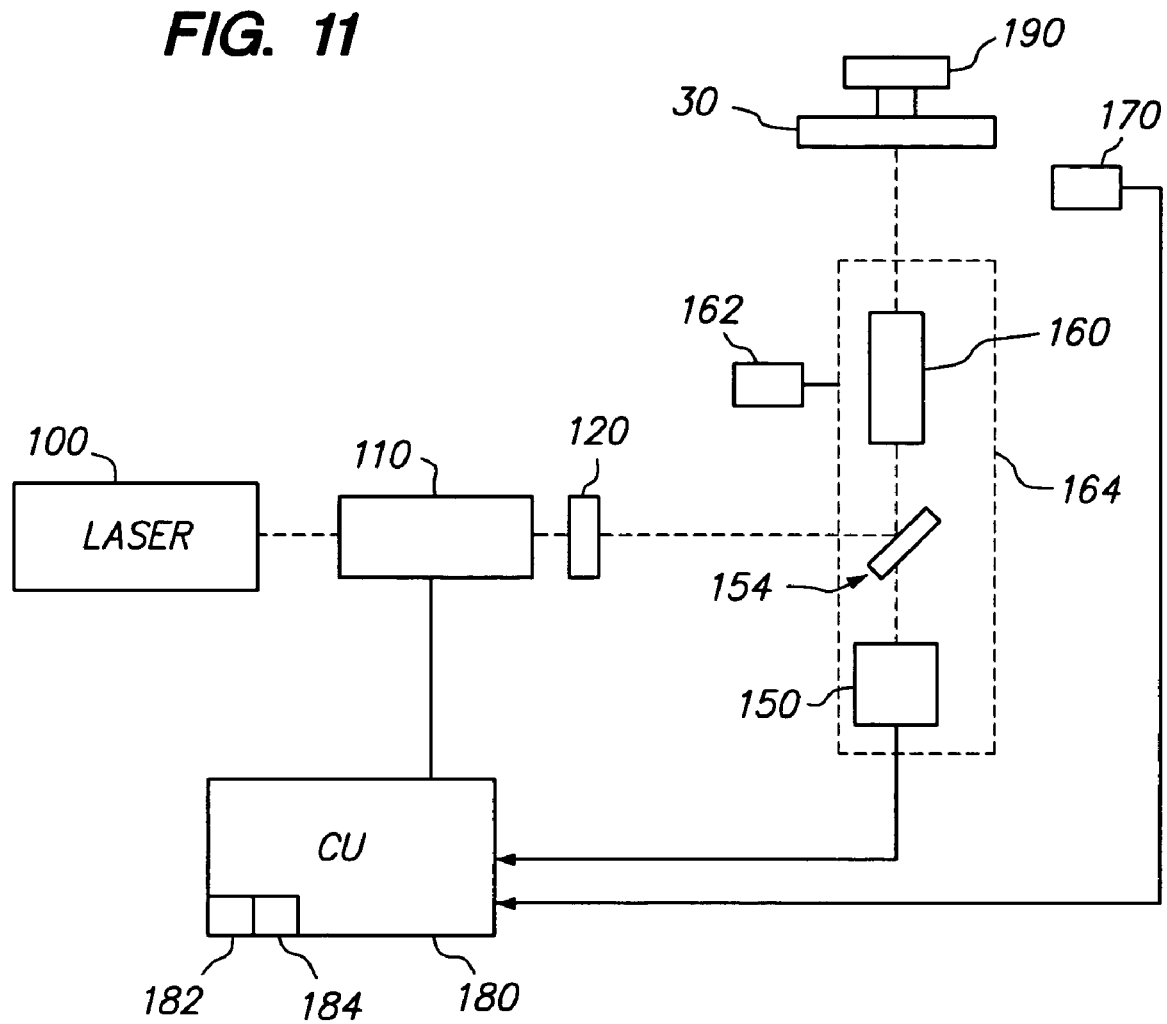
FIG. 11 illustrates an apparatus of the present invention.

Referring now to FIG. 11, an apparatus of the present invention (which may be generally referenced as an array "scanner") is illustrated with an array package 30 mounted therein. A light system provides light from a laser 100 which passes through an electro-optic modulator (EOM) 110 with attached polarizer 120. A control signal in the form of a variable voltage applied to the EOM 110 by the controller (CU) 180 changes the polarization of the exiting light which is thus more or less attenuated by the polarizer 120. Controller 180 may be or include a suitably programmed processor. Thus, EOM 110 and polarizer 120 together act as a variable optical attenuator which can alter the power of an interrogating light spot exiting from the attenuator. The remainder of the light transmitted by beam splitter 140 is in this case reflected off a dichroic beam splitter 154 and focused onto the array 12 of array package 30 using optical components in beam focuser 160. Light emitted from features 16 in response to the interrogating light, in particular fluorescence, is imaged, for example, using the same optics in focuser/scanner 160, and passes through the dichroic beamsplitter 154 and onto a detector (PMT) 150. More optical components (not shown) may be used between the dichroic and the PMT (lenses, pinholes, filters, fibers etc.) and the detector 150 may be of various different types (e.g. a photo-multiplier tube (PMT) or a CCD or an avalanche photodiode (APD)). A scanning system causes the interrogating light spot to be scanned across multiple sites on an array package 30 received in the apparatus, which sites include at least the multiple features 16 of the array. In particular the scanning system is typically a line by line scanner, scanning the interrogating light in a line across the array package 30, then moving ("transitioning") the interrogating light to begin scanning a timewise next row, scanning that timewise next row, and repeating the foregoing procedure row after row in accordance with any of the methods of the present invention (for example, any of those patterns in FIGS. 8–10). This can be accomplished by providing a housing 164 containing mirror 154, focuser 160, and detector 150, which housing 164 can be moved along a line of pixels (that is, from left to right or the reverse as viewed in FIG. 11) by transporter 162. In practice, detector 150 may be stationary with further suitable optics (for example, an additional mirror in housing 164) to allow this. A second direction of scanning can be provided by transporter 190 which moves array package 30 one or more lines 70 in a direction in and out of paper as viewed in FIG. 11. Transporter 190 may use a same or different actuator components to accomplish coarse (a larger number of lines) movement and finer movement (a smaller number of lines). For example, a first actuator (such as a linear or stepper motor) could accomplish coarse movement while a second actuator (such as a piezoelectric or electromagnetic pusher) could be used to provide the finer movement (for example, in a closed loop fashion or by driving between two mechanical stops).

The apparatus of FIG. 11 may further include a reader 170 which reads an identifier 54 from an array package 30. When identifier 54 is in the form of a bar code, reader 170 may be a suitable bar code reader.

Controller 180 of the apparatus is connected to receive fluorescent signals emitted in response to the interrogating light from emitted signal detector 130 and signals indicating a read identification from reader 170, and to provide the control signal to EOM 110. Controller 180 may also analyze, store, and/or output data relating to emitted signals received from detector 130 in a known manner. Controller 180 may include a computer in the form of a programmable digital processor, and include a media reader 182 which can read a portable removable media (such as a magnetic or optical disk), and a communication module 184 which can communicate over a communication channel (such as a network, for example the internet or a telephone network) with a remote site (such as a database at which information relating to array package 30 may be stored in association with the identification 54). Controller 180 is suitably programmed to execute all of the steps required by it during operation of the apparatus, as discussed further below. Alternatively, controller 180 may be any hardware or hardware/software combination which can execute those steps.

In one mode of operation, the array in package 30 is typically first exposed to a liquid sample introduced into the chamber through one of the septa 42, 50. The array may then be washed and scanned with a liquid (such as a buffer solution) present in the chamber and in contact with the array, or it may be dried following washing. Following a given array package 30 being mounted in the apparatus, reader 170 automatically (or upon operator command) reads array ID 54. Controller 180 can then use this ID 54 to retrieve information such as information which may aid in selecting a time between illuminating a line and illuminating a spatially closest later illuminated line based on an identifier associated with the array. Such information may include saturation characteristics of a chromophore, and other information, as already mentioned. Such information may be retrieved directly from the contents of ID 54 when ID 54 contains such information. Alternatively, ID 54 may be used to retrieve such information from a database containing the ID in association with such information. Such a database may be a local database accessible by controller 180 (such as may be contained in a portable storage medium in drive 182 which is associated with package 30, such as by physical association with package 30 when received by the user, or by a suitable identification), or may be a remote database accessible by controller 180 through communication module 184 and a suitable communication channel (not shown).

Next, the scanning system scans timewise successive lines 70 of pixels across the array in any of the methods of the present invention. During such a row scan, the EOM 110 may be controlled by controller 180 to turn off the illuminating light power at the array 12 during transitioning from line to line. This is repeated until the entire array 12 has been scanned.

Results from a sample exposed array, read according to a method of the present invention, may be raw results (such as fluorescence intensity readings for each feature in one or more color channels) or may be processed results such as obtained by rejecting a reading for a feature which is below a predetermined threshold and/or forming conclusions based on the pattern read from the array (such as whether or not a particular target sequence may have been present in the sample). The results of the reading (processed or not) may be forwarded (such as by communication of data representing the results) to a remote location if desired, and received there for further use (such as further processing).

Note that a variety of geometries of the features 16 may be constructed other than the organized rows and columns of the array of FIGS. 1–3. For example, features 16 can be arranged in a series of curvilinear rows across the substrate surface (for example, a series of concentric circles or semi-circles of spots), and the like. Even irregular arrangements of features 16 can be used, at least when some means is provided such that during their use the locations of regions of particular characteristics can be determined (for example, a map of the regions is provided to the end user with the array). Furthermore, substrate 10 could carry more than one array 12, arranged in any desired configuration on substrate 10. While substrate 10 is planar and rectangular in form, other shapes could be used with housing 34 being adjusted accordingly. In many embodiments, substrate 10 will be shaped generally as a planar, rectangular solid, having a length in the range about 4 mm to 200 mm, usually about 4 mm to 150 mm, more usually about 4 mm to 125 mm; a width in the range about 4 mm to 200 mm, usually about 4 mm to 120 mm and more usually about 4 mm to 80 mm; and a thickness in the range about 0.01 mm to 5.0 mm, usually from about 0.1 mm to 2 mm and more usually from about 0.2 to 1 mm. However, larger substrates can be used. Less preferably, substrate 10 could have three-dimensional shape with irregularities in first surface 11a. In any event, the dimensions of housing 34 may be adjusted accordingly. Additionally, during scanning it is possible to illuminate all pixels of a line simultaneously (for example, by using a line of light emitting diodes).

Various modifications to the particular embodiments described above are, of course, possible. Accordingly, the present invention is not limited to the particular embodiments described in detail above.

What is claimed is:

1. An apparatus for reading fluorescence signals from an array of chemical moieties, comprising:
    (a) an illumination source to cause fluorescence of the chemical moieties;
    (b) a scan system to direct the illumination source to different locations on the array; and
    (c) a detector to detect any resulting fluorescence from the array;
    (c) a processor which controls the scan system such that multiple locations on the array are illuminated and any resulting fluorescence detected, wherein a later illuminated location is spatially closer to an earlier illuminated location than is a temporally intervening illuminated location lying on a same line as the later and earlier illuminated locations.

2. An apparatus according to claim 1 wherein at least one later illuminated location is interleaved between previously illuminated locations.

3. An apparatus according to claim 1 wherein the processor additionally selects a time between illuminating a line and illuminating a spatially closest later illuminated line based on a saturation characteristic of a fluorophore producing the fluorescence.

4. An apparatus for reading fluorescence signals from an array of chemical moieties, comprising:
    (a) an illumination source to cause fluorescence of the chemical moieties;
    (b) a scan system to direct the illumination source to different locations on the array; and
    (c) a detector to detect any resulting fluorescence;
    (c) a processor which controls the scan system such that multiple paths across the array are illuminated and any resulting fluorescence detected, wherein the paths extend in a same lengthwise direction and are spaced from one another in a crosswise direction, and the spatial sequence of the paths does not correspond to their temporal sequence.

5. An apparatus according to claim 4 wherein at least one later illuminated path is closer to a an earlier illuminated path than a temporally intervening illuminated path.

6. An apparatus according to claim 5 wherein timewise successively illuminated paths are equally spaced crosswise from their respective closest later illuminated paths.

7. An apparatus according to claim 5 wherein at least one later illuminated path is interleaved between previously illuminated paths.

8. An apparatus according to claim 7 wherein multiple later illuminated paths are interleaved between previously illuminated paths.

9. An apparatus for reading fluorescence signals from an array of chemical moieties, comprising:
   (a) an illumination source to cause fluorescence of the chemical moieties;
   (b) a scan system to direct the illumination source to different locations on the array; and
   (c) a detector to detect any resulting fluorescence from the array;
   (c) a processor which controls the scan system such that multiple parallel lines across the array are illuminated and any resulting fluorescence detected, wherein a later illuminated line is closer to an earlier illuminated line than a temporally intervening illuminated line.

10. An apparatus according to claim 9 wherein multiple later illuminated lines are interleaved between previously illuminated lines.

11. An apparatus according to claim 10 wherein the spacing between the interleaved and previously illuminated lines is equal.

12. An apparatus of claim 9 additionally comprising repeating the illuminating in one or more further cycles, and wherein timewise successively illuminated lines of a cycle are illuminated by scanning a light beam in opposite directions.

13. An apparatus according to claim 9 wherein the processor additionally selects a time between illuminating a line and illuminating a spatially closest later illuminated line based on a saturation characteristic of a fluorophore producing the fluorescence.

14. An apparatus according to claim 9 wherein the processor additionally selects a time between illuminating a line and illuminating a spatially closest later illuminated line based on a spatial distribution of the illumination and a pixel size during the detecting.

15. A computer program product, comprising: a computer readable storage medium having a computer program stored thereon which, when loaded into a computer communicating with an apparatus for reading fluorescence signals from an array of chemical moieties, performs the steps of:
   illuminating multiple locations on the array and detecting any resulting fluorescence, wherein a later illuminated location is spatially closer to an earlier illuminated location than is a temporally intervening illuminated location lying on a same line as the later and earlier illuminated locations.

16. A computer program product according to claim 15 wherein at least one subsequently illuminated location is interleaved between previously illuminated locations.

17. A method according to claim 16 additionally comprising selecting a time between illuminating a location and illuminating a spatially closest later illuminated location based on a saturation characteristic of a fluorophore producing the fluorescence.

18. A computer program product, comprising: a computer readable storage medium having a computer program stored thereon which, when loaded into a computer communicating with an apparatus for reading fluorescence signals from an array of chemical moieties, performs the steps of:
   illuminating multiple parallel lines across the array and detecting any resulting fluorescence from the array, wherein a later illuminated line is closer to an earlier illuminated line than a temporally intervening illuminated line.

19. A method according to claim 18 wherein each line comprises a series of points illuminated sequentially by moving an illuminating beam along the line.

* * * * *